United States Patent [19]

Laguzza et al.

[11] Patent Number: 4,683,313

[45] Date of Patent: Jul. 28, 1987

[54] 2-ALKYL(OR PHENYL)THIO-6-N ALKYL ERGOLINES AND 4-DIALKYLAMINOTETRAHYDROBENZ[C,-D]INDOLES

[75] Inventors: Bennett C. Laguzza; Cynthia L. Nichols; Nicholas J. Bach, all of Indianapolis, Ind.

[73] Assignee: Eli Lilly and Company, Indianapolis, Ind.

[21] Appl. No.: 747,753

[22] Filed: Jun. 24, 1985

[51] Int. Cl.$^4$ ............... C07D 209/90; C07D 457/02; A61K 31/48
[52] U.S. Cl. ....................................... 548/437; 546/67
[58] Field of Search ................................ 548/437

[56] References Cited

U.S. PATENT DOCUMENTS 4,197,299  4/1980  Ferrari ........................... 424/248.52
4,229,450 10/1980  Ferrari ........................... 424/248.52
4,382,940  5/1983  Bernardi ............................. 424/261

OTHER PUBLICATIONS

Plieninger, et al., Chem. Abstracts, vol. 85 (1976), entry 108477e.

Primary Examiner—Donald G. Daus
Assistant Examiner—William A. Teoli, Jr.
Attorney, Agent, or Firm—Bruce J. Barclay; Leroy Whitaker

[57] ABSTRACT

D-2-Alkyl(or phenyl)thio-6-n-alkylergolines or ±-2-alkyl(or phenyl)thio-4-dialkylaminotetrahydrobenz[c,-d]indoles, dopamine D-1 antagonists.

2 Claims, No Drawings

2-ALKYL(OR PHENYL)THIO-6-N ALKYL ERGOLINES AND 4-DIALKYLAMINOTETRAHYDROBENZ[C,D]INDOLES

BACKGROUND OF THE INVENTION

Compounds based on the ergoline ring system:

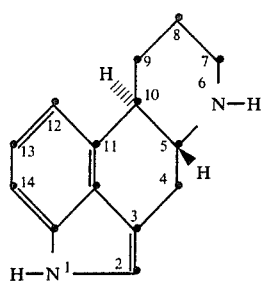

have a suprising variety of pharmaceutical activities. For example, many of the naturally occurring amides of lysergic acid, which is 8β-carboxy-6-methyl-9-ergolene, have valuable and unique pharmacologic properties. The trivial name "ergoline" is given to the above structure and the 9,10-double bonded compound—related to lysergic acid—is called a 9-ergolene rather than a 9,10-didehydroergoline. When the name D-ergoline is used herein in naming specific compounds, the letter "D" indicates that the C-5 carbon atom configuration has the absolute stereochemistry designated as R and that the hydrogen is β—above the plane of the ring system. However, modern usage has tended to omit the "D" on the ground that the newly synthesized ergolines or ergolenes are universally derivatives of natural products such as lysergic acid or elymoclavine, both of which have the R stereochemical —"D" series —configuration and in which the stereochemical integrity at C-5 is maintained during various synthetic procedures. In the ergolines, the C-10 hydrogen is alpha—below the plane of the ring, the C-5 C-10 ring junction being trans. It should be understood that all of the compounds disclosed herein have the R or β stereochemical configuration at C-5, whether or not the specific or generic name is preceded by a "D", and the α configuration at C-10.

Among the pharmacologically active amides of lysergic acid are included the naturally-occurring oxytoxic alkaloids ergocornine, ergokryptine, ergonovine, ergocristine, ergosine, ergotamine, etc., synthetic oxytocics such as methergine as well as the synthetic hallucinogen, lysergic acid diethylamide or LSD. The amides of 6-methyl-8-carboxyergoline (dihydrolysergic acid), known generically as the dihydroergot alkaloids, are oxytocic agents of lower potency and also lower toxicity than the ergot alkaloids themselves.

Recently, it has been found by Clemens, Semonsky, Meites, and their various co-workers that many ergot-related drugs have activity as prolactin inhibitors. Ergocornine, dihydroergocornine, 2-bromo α-ergokryptine and D-6-methyl-8-cyanomethylergoline (Semonsky et al U.S. Pat. No. 3,732,231) are examples of such drugs. References embodying some of the newer findings in the field of ergoline and ergolene chemistry include the following: Nagasawa and Meites, Proc. Soc. Exp't'l. Biol. Med., 135, 469 (1970); Lutterbeck et al., Brit. Med. J., 228, (July 24, 1971); Heuson et al., Europ. J. Cancer, 353 (1970); Coll. Czech. Chem. Commun., 33, 577 (1968); Nature, 221, 666 (1969); Seda et al., J. Reprod. Fert., 24, 263 (1971); Mantle and Finn, id, 441; Semonsky and co-workers, Coll. Czech. Chem. Comm., 36, 2200 (1971); Schaar and Clemens, Endocr., 90, 285-8 (1972); Clemens and Schaar, Proc. Soc. Exp. Biol. Med., 139, 659–662 (1972), Bach and Kornfeld, Tetrahedron Letters, 3225 (1974) and Sweeney, Clemens, Kornfeld and Poore, 64th Annual Meeting, American Association for Cancer Research, April 1973. Recently issued patents in the field of ergolines or of lysergic acid derivatives include the following: U.S. Pat. No. 3,923,812, U.S. Pat. No. 3,929,796, U.S. Pat. No. 3,944,582, U.S. Pat. No. 3,934,772, U.S. Pat. No. 3,954,988, U.S. Pat. No. 3,957,785, U.S. Pat. No. 3,966,739, U.S. Pat. No. 3,968,111, U.S. Pat. No. 4,001,242. Many other related and older patents can be found in Patent Office Classification Files 260-256.4 and 260-285.5.

U.S. Pat. No. 4,166,182 issued Aug. 28, 1979 (filed Feb. 8, 1978) discloses and claims D-6-n-propyl-8β-methylmercaptomethylergoline, among other compounds. The latter drug has been given the generic name "pergolide" and is presently undergoing clinical trial as a prolactin secretion inhibitor and in the treatment of Parkinsonism.

The use of pergolide, as a prolactin secretion inhibitor or in the treatment of Parkinsonism, is claimed in U.S. Pat. No. 4,180,582. The use of the corresponding 8α derivative in treating Parkinsonism is claimed in U.S. Pat. No. 4,246,265. 6-Ethyl-(or allyl)-8β-methylthiomethylergolines are claimed in U.S. Pat. No. 4,202,979.

Fuller et al, Life Sci., 24, 375 (1979) discusses the pharmacology of pergolide. The α adrenergic blocking activity of pergolide is summarized in Table 5, page 381.

6-Methyl-8β-methylthiomethylergolines are disclosed and claimed in U.S. Pat. Nos. 3,959,288 and 3,901,894 respectively as prolactin secretion inhibitors.

Ergolines which carry a C-2 alkylthio substituent are disclosed in several publications incuding Bernardi et al., U.S. Pat. No. 4,382,940 Mongegani et al., U.S. Pat. No. 4,321,361, (I) and 4,282,941 (II) Ferrari et al., U.S. Pat Nos. 4,197,299 (I) and 4,229,450 (II). No example of a (±)-2-alkylthio-1,3,5,6-benz[c,d]indole has been found.

Dopamine D-1 antagonists are not known.

DESCRIPTION OF THE INVENTION

This invention provides compounds of the following two formulas:

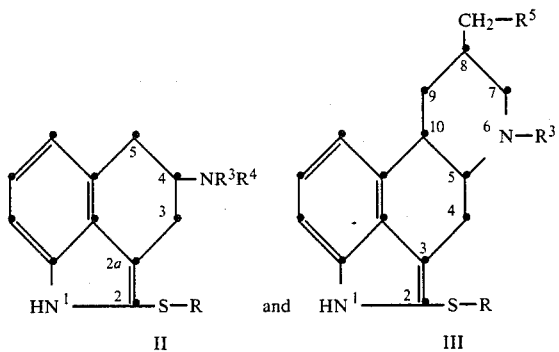

wherein R is $C_{1-3}$ alkyl or phenyl, $R^3$ and $R^4$ are individually methyl, ethyl or n-propyl; $R^5$ is CN, S—$R^3$ or SO—R³; and pharmaceutically-acceptable, acid addition salts thereof.

Compounds according to formula II are named as (±)-2-alkyl(or phenyl)thio-4-dialkylamino-1,3,4,5-tetrahydrobenz[c,d]indoles. Compounds according to formula III are named as substituted D-ergolines; ie, D-2-$C_{1-3}$ alkyl(or phenyl)thio-6-alkyl-8-substituted-ergolines. Ergolines have 3 asymmetric centers, at carbons 5, 8 and 10. The term "D" however, provides the trans configuration at C-5 and C-10; ie, the hydrogen at C-5 is beta and at C-10 alpha. Thus, the orientation at only one of these three centers, at C-8, is not specified. The $CH_2$—R⁵ substituent at C-8 can be either alpha or beta. Since the two C-8 products are diastereoisomers, not mirror images, they can be separated mechanically. The orientation of the $CH_2$—R⁵ group is ordinarily specified in the starting material used (V below).

Compounds according to II above have a center of asymmetry; specifically, at C-4, a dialkylamino group. These compounds occur as racemates (designated by the symbol "±") composed of two diastereoisomers, the (−) and (+) enantiomers. Racemates according to II can be separated into their individual enantiomorphs by procedures to be found in references such as Jacques et al., *Enantiomers, Racemates and Resolutions* (John Wiley and Sons, New York 1981). This reference contains descriptions of the procedure used to find a resolving agent using the trial and error method. It also tells how to carry out a resolution after finding a resolving agent (in this instance, an optically-active acid capable of yielding an insoluble salt with a free base according to II).

Pharmaceutically-acceptable acid addition salts of the compounds of this invention include salts derived from non-toxic inorganic acids such as: hydrochloric acid, nitric acid, phosphoric acid, sulfuric acid, hydrobromic acid, hydriodic acid, phosphorous acid and the like, as well as salts derived from non-toxic organic acids such as aliphatic mono and dicarboxylic acids, phenyl-substituted alkanoic acids, hydroxy alkanoic and alkandioic acids, aromatic acids, aliphatic and aromatic sulfonic acids, etc. Such pharmaceutically-acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, glucohepanoate, lactobionate, methanesulfonate, propanesulfonate, naphthalene-1-sulfonate naphthalene-2-sulfonate and the like salts.

Typical compounds coming within the scope of formula II and III above include
D-2-methylthio-6-ethyl-8β-cyanomethylergoline maleate
D-2-n-propylthio-6-methyl-8β-methylthiomethylergoline succinate
D-2-phenylthio-6-methyl-8β-n-propylthiomethylergoline tartrate
D-2-n-propylthio-6-n-propyl-8β-cyanomethylergoline hydrochloride
D-2-isopropylthio-6-methyl-8β-methylthiomethylergoline sulfate
(±)-2-phenylthio-4-diethylamino-1,3,4,5-tetrahydrobenz[c,d]indole methanesulfonate
(±)-2-ethylthio-4-methylethylamino-1,3,4,5-tetrahydrobenz[c,d]indole lactate
(±)-2-isopropylthio-4-methyl-n-propylamino-1,3,4,5-tetrahydrobenz[c,d]indole benzoate
(±)-2-n-propylthio-4-di-n-propylamino-1,3,4,5-tetrahydrobenz[c,d]dindole citrate.
(±)-2-phenylthio-4-dimethylamino-1,3,4,5-tetrahydrobenz[c,d]indole ethanesulfonate Compounds according to II or III are prepared by reacting compounds of structures IV or V below

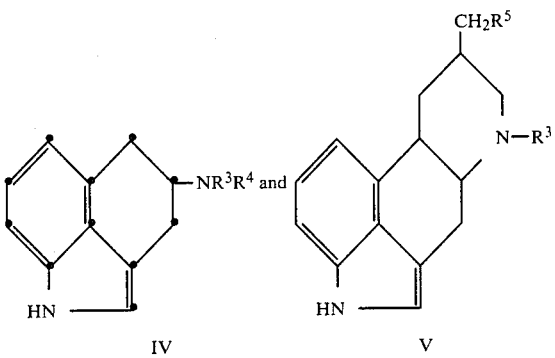

wherein R³, R⁴ and R⁵ have their previous meaning, with a $C_{1-3}$ alkyl(or phenyl)sulfenylchloride in a mutual anhydrous solvent (DMF) at subzero temperatures, below about −10° C., preferably at −65° C. to −75° C. The desired compounds are isolated by standard procedures and purified by chromatography of the base or crystallization of an acid addition salt. The sulfenyl chloride is prepared by the reaction of dimethylsulfide with sulfuryl chloride ($SO_2Cl_2$) according to the procedure of Harpp et al., *Synthesis*, 181 (1979).

The starting materials IV and V are available directly or by adaptation of the procedures set forth in one or more of the following references; U.S. Pats. Nos. 3,732,231, 3,901,894, 4,246,265, 4,166,182, 4,180,582, 4,202,979, 4,110,399; Stoll, et al., *Helv. Chim. Actai*, 35 148 (1952); Kornfeld et al, *J. Am. Chem. Soc.*, 78, 3087 (1956), Cassady et al, *J. Med. Chem.* 17, 300 (1974);

This invention is further illustrated by the following specific Examples.

EXAMPLE 1

Preparation of
D-2-methylthio-6-methyl-8-cyanomethylergoline

A solution of 3.6 mM sulfenyl chloride in methylenedichloride was made by adding 0.16 ml of sulfuryl chloride to a solution of 0.16 ml of methyldisulfide and 5 ml of methylenedichloride. Three drops of triethylamine were added. The above reaction was carried out at −10° C. under a nitrogen atmosphere. The reaction mixture was stirred for 5 minutes at −10° C., and then allowed to warm to room temperature for about 30 minutes. At this point, a solution of D-6-methyl-8-cyanomethylergoline (0.93 g in 50 ml of anhydrous DMF) was chilled to a temperature in the range −45° C. to −50° C. The sulfenyl chloride solution was added in dropwise fashion. The resulting reaction mixture was allowed to warm to room temperature slowly overnight. The reaction mixture, a slurry, was poured into aqueous ammonium hydroxide and the alkaline aqueous solution extracted 3 times with equal volumes of methylenedichloride. Methylenedichloride extracts were combined and the combined extracts washed with brine and then dried. Evaporation of the solvent yielded a residue weighing about 1 gram. This residue was chromatographed over silica using 19:1 chloroform/methanol as the eluant. Fractions containing the desired 2-methylthio product were combined and rechromatographed using chloroform containing 1% methanol as the eluant. Fractions shown to contain D-2-methylthio-6-methyl-8-cyanomethylergoline by TLC were combined to yield 150 mg of a foam. This foam was recrystallized from an ether/hexane solvent mixture to yield 100 mg of yellow/orange crystals: One spot by TLC: $R_f=0.44$ (9:1 chloroform/methanol). The compound melted at about 173° C.; Mass spectrum: molecular ion at 311.

Analysis calculated: C, 69.42; H, 6.80; N 13.49;
Found: C, 69.57; H, 6.92; N 13.75.

EXAMPLE 2

Preparation of
(±)-2-Methylthio-4-dimethylamino-1,3,4,5-tetrahydrobenz[c,d]indole A solution of 4.8 mM sulfenyl chloride in methylenedichloride prepared as in Example 1 was added in portions to a solution of 0.96 g of (±)-4-dimethylamino-1,3,4,5-tetrahydrobenz[c,d] indole in anhydrous DMF to a temperature in the range of −40° C. to −50° C. After the reaction had warmed to room temperature, it was poured into dilute aqueous ammonium hydroxide and the alkaline mixture extracted with methylenedichloride. The product was worked up and isolated by the procedure of Example 1 to yield a residue which was 2 spot material, weight=240 mg. The residue was dissolved in methanol an a methanol solution of 0.116 g of maleic acid added. The solution was filtered and the solvent removed in vacuo. The residual oil was not soluble in ether; so sufficient methanol was added to dissolve the oil. Scratching produced crystalline product comprising (±)-2-methylthio-4-dimethyamino-1,3,4,5-tetrahydrobenz[c,d]indole maleate; mp=164.5°-7° C.

Analysis calculated: C, 59.65; H, 6.12; N 7.73;
Found: C, 59.68; H, 6.15; N 7.49.

EXAMPLE 3

Preparation of D-2-methylthio-6-methyl-8-methyl mercaptomethylergoline

Following the procedure of Example 1, 1 g of D-6-methyl-8-β-methylthiomethylergoline (from U.S. Pat. No. 3,901,894) was dissolved in anhydrous DMF. A solution of 3.8 mM sulfenyl chloride (prepared by adding 0.17 ml of sulfuryl chloride to a solution of 0.17 ml of methyldisulfide in 10 ml of anhydrous methylenedichloride at dry/ice-acetone temperatures) was added in dropwise fashion under a positive nitrogen pressure. The reaction temperature was maintained between −65° C. and −70° C. using dry/ice-acetone cooling bath. The reaction mixture was allowed to come to room temperature, at which temperature it was stirred overnight under nitrogen. The reaction mixture, a slurry, was poured into 50 ml of 5% aqueous ammonium hydroxide and the alkaline solution extracted thorougly with methylenedichloride. The methylenedichloride extracts were combined and the combined extracts washed with brine and then dried. Chromatography over silica using chloroform containing 1% methanol as the eluant yielded fractions containing a material with $R_f=0.41$ in 19:1 methylenedichloride/methanol, which material was indicated by nmr to be a 1,2-di(methylthio)derivative. The compound was therefore dissolved in 0.2N aqueous hydrochloric acid containing sufficient methanol to maintain the material in solution. This mixture was heated on a steam bath in order to remove the N-methylthio (1-methylthio) group. After heating for about 30 minutes, the reaction mixture was made basic by the addition of 10% aqueous ammonium hydroxide and the alkaline layer extracted 3 times with an equal volume of methylenedichloride. The methylenedichloride extracts were combined, washed with brine and then dried over anhydrous sodium sulfate. Evaporation of the solvent yielded about 90 mg of a crude product which NMR indicated was D-2-methylthio-6-methyl-8β-methylthiomethylergoline. This crude product was rechromatogrpahed over silica using the same eluant. Fractions shown to contain the desired material by TLC were combined and the solvent evaporated therefrom, yielding a residual oil. The oil was dissolved in ether and crystallization induced by the addition of hexane. 29 mg of yellow crystals were obtained comprising purified D-2-methylthio-6-methyl-8β-methylthiomethylergoline: Molecular ion at 332 by mass spectroscopy.

The preparation of pharmaceutically-acceptable acid addition salts of the compounds of this invention, particularly the maleate salt, is illustrated in the above examples. Generally speaking, an equivalent of the free base in a nonpolar organic solvent, such as ether, can be mixed with an equivalent of the acid, also in ether. The salt is usually insoluble in the solvent system and is recovered by filtration. Alternatively, a solution of an equivalent of the free base represented by II or III in a lower alkanol is mixed with an equivalent of the acid, also in solution in a lower alkanol. In this variation, the salt is recovered by evaporation of the solvent and purified by recrystallization.

The compounds of this invention are dopamine D-1 antagonists without D-2 agonist activity; i.e., they counter the effects of dopamine at D-1 receptors in the brain. The dopamine D-1 antagonist assay was carried out as follows.

RETINAL ADENYLATE CYCLASE ASSAY

Adult male, Sprague-Dawley rats purchased from Charles River Breeding Laboratories (North Wilmington, MA) were used in these studies. The rats were decapitated and the eyeballs were removed. The eyeballs were bisected at the juncture of the sclera and iris using capsulotomy scissors. The retina was dissociated from the choroid by irrigation with saline. Retinal tissue was removed from the eyeball and homogenized with Tris-2 mM EGTA (pH 7.4; 1:150 wt.:vol.) using a Teflon-glass Dounce homogenizer at a speed of 50 rpm.

The adenylate cyclase assay was performed at an incubation temperature of 30° C. and over a 20-minute reaction period. The reaction mixture contained the following constant ingredients: 2 nM MgSO$_4$, 0.5 mM EGTA, 1 mM IBMX, 0.01 mM GTP, 80 mM Tris-HCl, pH 7.4, 0.5 mM ATP with 3-5 $\times 10^6$ cpm $^{32}$P-ATP and 20-25 µg retinal homogenate protein. The reaction mixture also contained various concentrations of the compound tested alone or in the presence of 10 µM dopamine. The reaction was started by the addition of ATP/$^{32}$P-ATP and was stopped by the addition of a solution containing 1% SDS, 20 mM ATP, 0.7 mM cyclic AMP, 80 mM Tris-HCl pH 7.4 and $10^4$ cpm $^3$H-cyclic AMP in a total volume of 200 μl. This mixture was heated for 2 minutes at 90° C. to further insure reaction termination. The $^{32}$P cyclic AMP formed during the reaction was isolated from each sample using the chromatographic method of Solomon (1979). The $^3$H-cyclic AMP was also simultaneously isolated with this procedure. The net $^{32}$P-cyclic AMP formed was calculated by correcting the final $^{32}$P cpm for column recovery efficiency determined by the $^3$H recovery and for background radioactivity determined by the radioactivity in incubates without homogenate. Homogenate protein determinations were made using the BioRad protein assay with bovine serum albumin used at the reference protein. Dopaminergic agonist activity was evaluated based upon percent stimulation over activity without drug. Dopaminergic antagonist activity was estimated based upon the percent inhibition of the responsed to 10 μM dopamine.

The results of this determination are given in Table 1 below. In the Table, column 1 gives the name of the compound, column 2, the concentration of drug in the medium, and column 3, the percent inhibition of 10 μM dopamine.

TABLE 1

| Name | Concentration μM | % Inhibition of 10 μM dopamine |
|---|---|---|
| (±)-2-methylthio-6- | 0.1 | −5. ± 9.5 |
| methyl-8-methylthio | 1.0 | 26.4 ± 6.0 |
| methylergoline | 3.0 | 49.0 ± 0.8 |
|  | 10.0 | 72.5 ± 4.8 |
|  | 30.0 | 73.8 ± 4.2 |
|  | 100.0 | 76.6 ± 7.7 |
| (±)-2-methylthio-4- | 0.1 | −5.3 |
| dimethylamino-1,3,4,5- | 0.3 | −2.2 ± 3.8 |
| tetrahydrobenz[c,d]- | 1.0 | 0.9 ± 1.5 |
| indole maleate | 3.0 | 19.1 ± 6.4 |
|  | 10.0 | 34.7 ± 13.0 |
|  | 100.0 | 84.0 ± 3.3 |

The drugs of this invention, represented by formulas II and III, are shown to lack D-2 dopamine agonist activity at D-1 antagonist dose levels in a test to determine their ability (or inability) to inhibit the secretion of prolactin in nonrespernized rats. This test was carried out as follows.

Adult male rats of the Sprague-Dawley strain weighing about 200 g. were housed an air-conditioned room with controlled lighting (14 hours light-10 hours dark) and fed lab chow and water ad libitum. The compound was dissolved in 10 percent ethanol, and injected intraperitoneally at a dose of 1 or 2 mg/kg. The compound was administered to a group of 10 rats, and a control group of 10 intact males received an equivalent amount of 10 percent ethanol. One hour after treatment, all rats were killed by decapitation, and 150 μl aliquots of serum were assayed for prolactin.

The difference between the mean prolactin level of the treated rats and mean prolactin level of the control rats, divided by the mean prolactin level of the control rats, gives the percent change in prolactin secretion attributable to the given dose.

The results of this determination are given in the following Table.

TABLE II

| Name of Compound | Dose mg/kg | Percent changes in prolactin |
|---|---|---|
| D-2-methylthio-6-methyl-8-cyanomethyl-ergoline | 2 | 68% inhibition* |
| D-2-methylthio-6-methyl-8-methylthio-methylergoline | 2 | 54% stimulation* |
| (±)-2-methylthio-4-dimethylamino-1,3,4,5-tetrahydrobenz[c,d]indole maleate | 1 | 9% inhibition |

*statistically significant at $p < 0.05$

The compounds of this invention are usually administered for therapeutic purposes as antidopamine D-1 agents in a variety of oral formulations as illustrated below.

Hard gelatin capsules are prepared using the following ingredients:

|  | Quantity (mg./capsule) |
|---|---|
| Active compound | .1–20 mg |
| Starch dried | 200 |
| Magnesium stearate | 10 |

The above ingredients are mixed and filled into hard gelatin capsules.

A tablet formulation is prepared using the ingredients below:

|  | Quantity (mg./tablet) |
|---|---|
| Active compound | .1–20 mg |
| Cellulose, microcrystalline | 400 |
| Silicon dioxide, fumed | 10 |
| Stearic acid | 5 |

The components are blended and compressed to form tablets.

Alternatively, tablets each containing 0.1–2 mg. of active ingredient are made up as follows:

| Active ingredient | .1–20 mg. |
|---|---|
| Starch | 45 mg. |
| Microcrystalline cellulose | 35 mg. |
| Polyvinylpyrrolidone (as 10% solution in water) | 4 mg. |
| Sodium carboxymethyl starch | 4.5 mg. |
| Magnesium stearate | 0.5 mg. |
| Talc | 1 mg. |

The active ingredient, starch and cellulose are passed through a No. 45 mesh U.S. sieve and mixed thoroughly. The solution of polyvinylpyrrolidone is mixed with the resultant powders which are then passed through a No. 14 U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed with a tablet machine to yield tablets.

Capsules each containing 0.1–2 mg. of medicament are made as follows:

| Active ingredient | .1–20 mg. |
|---|---|

| | |
|---|---|
| Starch | 59 mg. |
| Microcrystalline cellulose | 59 mg. |
| Magnesium stearate | 2 mg. |

The active ingredient, cellulose, starch and magnesium stearate are blended, passed through a No. 45 mesh U.S. sieve, and filled into hard gelatin capsules.

Suspensions each containing 0.1–2 mg. of medicament per 5 ml. dose are made as follows:

| | |
|---|---|
| Active ingredient | .1–20 mg. |
| Sodium carboxymethyl cellulose | 50 mg. |
| Syrup | 1.25 ml. |
| Benzoic acid solution | 0.10 ml. |
| Flavor | q.v. |
| Color | q.v. |
| Purified water to | 5 ml. |

The medicament is passed through a No. 45 mesh U.S. sieve and mixed with the sodium carboxymethylcellulose and syrup to form a smooth paste. The benzoic acid solution, flavor and color are diluted with some of the water and added with stirring. Sufficient water is then added to produce the required volume.

Dopamine D-1 antagonists are useful in the field of mental health. For oral administration as a neuroleptic or antipsychotic agent, tablets, capsules or suspensions containing from about 0.1 to about 2 mg. of active drug per dose are given 3–4 times a day, giving a daily dosage of 0.3 to 8 mgs. or, for a 75 kg. person, about 2.25 to about 600 mg./per day. The intravenous dose is in the range from about 0.1 to about 100 mcg./kg. For oral administration, dose levels of from 1.0–20 mg per kg are employed with a concomitant 10-fold increase in daily dose levels.

I claim:

1. A compound of the formula:

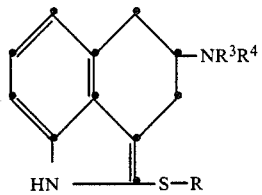

II wherein R is $C_{1-3}$ alkyl or phenyl and $R^3$ and $R^4$ are individually methyl, ethyl or n-propyl; and pharmaceutically-acceptable, acid-addition salts thereof.

2. A compound according to claim 1, said compound being (±)-2-methylthio-4-dimethylamino-1,3,4,5-tetrahydrobenz[c,d]indole.

* * * * *